(12) United States Patent
Hu et al.

(10) Patent No.: US 11,534,591 B2
(45) Date of Patent: Dec. 27, 2022

(54) SYSTEMS AND METHODS FOR FACILITATING INSTRUMENT DELIVERY THROUGH A PERIPHERAL INTRAVENOUS CATHETER

(71) Applicant: Becton, Dickinson and Company, Franklin Lakes, NJ (US)

(72) Inventors: Olivia Hu, Shanghai (CN); Yiping Ma, Layton, UT (US); Curtis H. Blanchard, Riverton, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 540 days.

(21) Appl. No.: 16/511,316

(22) Filed: Jul. 15, 2019

(65) Prior Publication Data

US 2020/0023176 A1    Jan. 23, 2020

Related U.S. Application Data

(60) Provisional application No. 62/699,520, filed on Jul. 17, 2018.

(51) Int. Cl.
*A61M 25/00* (2006.01)
*A61M 39/02* (2006.01)
(Continued)

(52) U.S. Cl.
CPC ... *A61M 39/0247* (2013.01); *A61B 5/150992* (2013.01); *A61B 5/6852* (2013.01); *A61M 5/14* (2013.01); *A61M 25/0097* (2013.01); *A61M 25/09* (2013.01); *A61M 39/06* (2013.01); *A61B 5/15003* (2013.01); *A61M 2039/0202* (2013.01); *A61M 2039/0205* (2013.01);
(Continued)

(58) Field of Classification Search
CPC .... A61M 2039/027; A61M 2039/0273; A61M 2039/0279; A61M 2039/062; A61M 203/0633; A61M 2039/064; A61M 2039/0646; A61M 2039/0653; A61M 2039/066; A61M 2039/0666
See application file for complete search history.

(56) References Cited

U.S. PATENT DOCUMENTS 4,058,121 A * 11/1977 Choksi ............... A61J 1/2096
                                                    604/416
4,387,879 A *  6/1983 Tauschinski ...... A61M 39/0693
                                                    604/249
(Continued)

FOREIGN PATENT DOCUMENTS

JP        5253534      7/2013
WO     2016/168745    10/2016

*Primary Examiner* — William R Carpenter
(74) *Attorney, Agent, or Firm* — Kirton McConkie; Whitney Blair; Kevin Stinger (57) ABSTRACT

A system for facilitating instrument delivery through a peripheral intravenous catheter may include a catheter adapter having a proximal end, a distal end, and a lumen extending there through. The catheter adapter may include a side port. The system may include an extension tube extending from the side port. The system may include a blood control valve disposed in the lumen of the catheter adapter. The system may include a peripheral intravenous catheter extending distally from the catheter adapter.

16 Claims, 10 Drawing Sheets

(51) Int. Cl.
*A61B 5/15* (2006.01)
*A61M 25/09* (2006.01)
*A61B 5/00* (2006.01)
*A61M 5/14* (2006.01)
*A61M 39/06* (2006.01)

(52) U.S. Cl.
CPC .............. *A61M 2039/027* (2013.01); *A61M 2039/0258* (2013.01); *A61M 2039/0273* (2013.01); *A61M 2039/0279* (2013.01); *A61M 2039/0285* (2013.01)

(56) References Cited

U.S. PATENT DOCUMENTS

| | | | | |
|---|---|---|---|---|
| 4,559,043 A * | 12/1985 | Whitehouse | .......... | A61M 39/14 604/201 |
| 5,139,483 A * | 8/1992 | Ryan | .......... | A61M 39/1011 604/905 |
| 5,405,340 A * | 4/1995 | Fageol | .......... | A61M 39/1011 285/247 |
| 5,697,914 A * | 12/1997 | Brimhall | .......... | A61M 25/0631 604/177 |
| 5,860,962 A * | 1/1999 | Lewandowski | ..... | A61M 39/045 604/263 |
| 6,117,108 A | 9/2000 | Woehr et al. | | |
| 8,066,670 B2 | 11/2011 | Cluff et al. | | |
| 8,496,623 B2 | 7/2013 | Burkholz | | |
| 9,399,120 B2 | 7/2016 | Burkholz | | |
| 9,750,446 B2 | 9/2017 | Devgon | | |
| 2002/0177814 A1 * | 11/2002 | Meng | .......... | A61M 25/06 604/164.07 |
| 2008/0200904 A1 * | 8/2008 | Cluff | .......... | A61M 39/20 604/537 |
| 2011/0016302 A1 * | 1/2011 | Amou | .......... | G06F 11/1417 713/2 |
| 2011/0046570 A1 * | 2/2011 | Stout | .......... | A61M 39/0693 604/246 |
| 2012/0016302 A1 * | 1/2012 | Stout | .......... | A61M 25/0693 604/122 |
| 2012/0022502 A1 * | 1/2012 | Adams | .......... | A61M 25/005 604/526 |
| 2012/0197200 A1 * | 8/2012 | Belson | .......... | A61M 25/06 604/164.12 |
| 2013/0090607 A1 * | 4/2013 | McKinnon | .......... | A61M 39/0693 604/247 |
| 2013/0090608 A1 * | 4/2013 | Stout | .......... | A61M 39/00 29/525.08 |
| 2013/0237925 A1 * | 9/2013 | Trainer | .......... | A61M 25/0606 604/247 |
| 2014/0364809 A1 | 12/2014 | Isaacson et al. | | |

\* cited by examiner

SYSTEMS AND METHODS FOR FACILITATING INSTRUMENT DELIVERY THROUGH A PERIPHERAL INTRAVENOUS CATHETER

RELATED APPLICATIONS

This application claims the benefit of U.S. Application No. 62/699,520, filed Jul. 17, 2018, and entitled SYSTEMS AND METHODS FOR FACILITATING INSTRUMENT DELIVERY THROUGH A PERIPHERAL INTRAVENOUS CATHETER BACKGROUND, which is incorporated herein in its entirety.

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the blood vessel, a user generally confirms that there is "flashback" of blood in a flashback chamber of a PIVC assembly. Once placement of the needle has been confirmed, the user may temporarily occlude flow in the vasculature and remove the introducer needle, leaving the PIVC in place for future blood withdrawal and/or fluid infusion.

Currently, there may be several limitations to the use of a PIVC for fluid infusion and blood draw. The PIVC may narrow, collapse, or clog with time, leading to failure of the PIVC. Due to this, PIVCs may often be used for acquiring a blood sample at a time of PIVC placement, but they are much less frequently used for acquiring a blood sample during the PIVC dwell period. Therefore, when a blood sample is needed, an additional needle stick may be used to provide vein access for blood collection, which may be painful for the patient. In order to extend the life of the PIVC and allow for fluid infusion and/or blood withdrawal through the PIVC assembly, in some instances, an instrument delivery device may be used to deliver an additional catheter through the PIVC.

Delivery of the additional catheter through the PIVC may be difficult in current integrated catheter systems having an integrated extension tube, such as, for example, the BD NEXIVA™ Closed IV Catheter System, the BD NEXIVA™ DIFFUSICS™ Closed IV Catheter System, the Becton Dickinson PEGASUS™ Safety Closed IV Catheter System, or other integrated catheter systems. In further detail, it may be difficult to advance the additional catheter through a length of the integrated extension tube and/or through a septum disposed in a lumen of a catheter adapter of the system in order to place the additional catheter within or beyond the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to devices, systems, and methods for facilitating delivery of an instrument through a PIVC. In some embodiments, the instrument may include an additional catheter for fluid infusion or blood draw, a guidewire, a probe with a sensor, or a light tube for disinfection. In some embodiments, a system for facilitating instrument delivery through the PIVC may include a catheter adapter, which may include a proximal end, a distal end, and a lumen extending there through. In some embodiments, the PIVC may extend distally from the catheter adapter. In some embodiments, the catheter adapter may include a side port. In some embodiments, an extension tube may extend from the side port. In some embodiments, a blood control valve may be disposed in the lumen of the catheter adapter.

In some embodiments, the blood control valve may be disposed proximal to the side port. In these and other embodiments, the blood control valve may not allow air venting. In some embodiments, the blood control valve may be disposed distal to the side port. In these and other embodiments, the blood control valve may allow air venting.

In some embodiments, the system may include a Y-adapter coupled to a proximal end of the extension tube. In some embodiments, the Y-adapter may include a first port and a second port. In some embodiments, a needleless connector may be coupled to the first port, and a needleless connector may be coupled to the second port. In these and other embodiments, the blood control valve may allow air venting, which may facilitate observation of blood flashback by the user.

In some embodiments, the system may include a cap, which may be coupled to the proximal end of the catheter adapter. In some embodiments, the system may include a needleless connector coupled to the proximal end of the catheter adapter.

In some embodiments, the proximal end of the catheter adapter may include a luer adapter or a non-luer adapter. In some embodiments, an extension set may be coupled to the proximal end of the catheter adapter. In some embodiments, the extension set may include a distal connector coupled to the proximal end of the catheter adapter, and a proximal connector. In some embodiments, the extension set may include tubing disposed between the distal connector and the proximal connector. In some embodiments, the proximal connector may include a needleless connector.

In some embodiments, the distal connector may include a cannula that penetrates the blood control valve in response to the distal connector being coupled to the proximal end of the catheter adapter. In some embodiments, the cannula may be blunt. In some embodiments, the cannula may be constructed of plastic or metal, such as, for example, steel.

In some embodiments, the distal connector may include a male luer, which may provide a fluid tight seal. In some embodiments, the male luer may include an extension, which may penetrate the blood control valve in response to the distal connector being coupled to the proximal end of the catheter adapter. In some embodiments, the extension and/or the cannula may include one or more flushing windows. In some embodiments, the cannula and the extension may each correspond to an actuator of the blood control valve. In some embodiments, the lumen of the catheter adapter may not include an actuator of the blood control valve other than the cannula or the extension.

In some embodiments, the system may include an instrument delivery device, which may be coupled to the proximal end of the catheter adapter. In some embodiments, the instrument delivery device may include the instrument, which may be configured to advance distally through the blood control valve and the PIVC. In some embodiments, a distal portion of the lumen of the catheter adapter may be narrowed to provide a guide feature for the instrument as the instrument is advanced distally.

In some embodiments, the system may include a needle assembly removably coupled to the proximal end of the catheter adapter. In some embodiments, an introducer needle of the needle assembly may extend through the blood control valve.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

The present disclosure relates generally to devices, systems, and methods for facilitating delivery of an instrument through a PIVC. In some embodiments, the instrument may include an additional catheter for fluid infusion or blood draw, a guidewire, a probe with a sensor, or a light tube for disinfection.

Figure 1A:
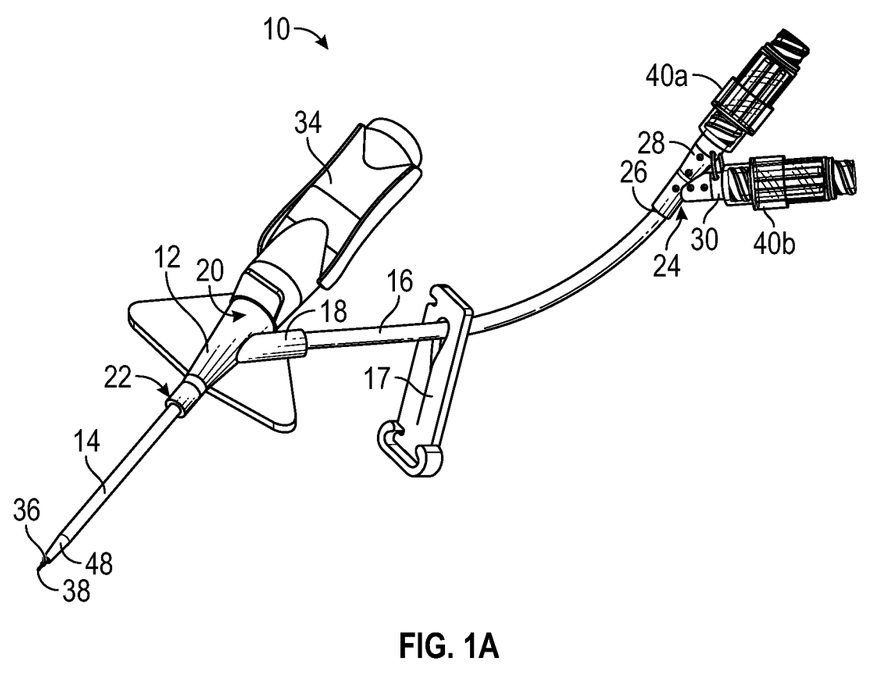
FIG. 1A is an upper perspective view of an example catheter system, illustrating an example needle assembly coupled to a proximal end of an example catheter assembly, according to some embodiments.

Referring now to FIG. 1A, in some embodiments, a system 10 for facilitating instrument delivery through a PIVC 14 may include a catheter adapter 12, the PIVC 14 extending distally from the catheter adapter 12, and an extension tube 16 extending from the catheter adapter 12. In some embodiments, the catheter adapter 12 may include a side port 18. In some embodiments, the extension tube 16 may extend from the side port 18. In some embodiments, the catheter adapter 12 may include a proximal end 20 and a distal end 22.

In some embodiments, the system 10 may include a Y-adapter 24, which may include a distal end 26, a first port 28, and a second port 30. In some embodiments, the distal end 26 of the Y-adapter 24 may be coupled to the extension tube 16. In some embodiments, the extension tube 16 may include a clamp 17, which may selectively close off the extension tube 16 to prevent blood or another fluid from flowing through the extension tube 16.

In some embodiments, the system 10 may be integrated, having the integrated extension tube 16. In other embodiments, the system 10 may be non-integrated. In some embodiments, the system 10 may include a needle assembly, which may include a needle hub 34 and an introducer needle 36. In some embodiments, in response to the introducer needle 36 being inserted into a vein of the patient, flashback of blood may flow through a sharp distal tip 38 of the introducer needle 36 and out of a distal notch of the introducer needle 36 into a portion of the system 10. For example, the blood flashback may flow through the distal tip 38 and out of the distal notch into a space between an exterior surface of the introducer needle 36 and an interior surface of the PIVC 14 (this may be referred to as "primary flashback"). In some embodiments, blood flashback may flow into the extension tube 16 (this may be referred to as "secondary flashback"). Primary and/or secondary blood flashback may confirm that the introducer needle 36 and/or a distal tip 48 of the PIVC 14 are located within the vein of the patient. In some embodiments, the needle assembly may be removably coupled to the proximal end 20 of the catheter adapter 12. In some embodiments, the introducer needle 36 of the needle assembly may extend through the blood control valve 44.

In some embodiments, a first needleless connector 40a may be coupled to the first port 28, and/or a second needleless connector 40b may be coupled to the second port 30. In these and other embodiments, a blood control septum or valve disposed within the lumen 46 of the catheter adapter 12 may allow air venting. Some non-limiting examples of needleless connectors are described in U.S. Pat. No. 8,066, 670, filed Nov. 5, 2007, entitled "VASCULAR ACCESS DEVICE SEPTUM VENTING," which is hereby incorporated by reference. In some embodiments, the system 10 may not include a vent-plug. In some embodiments, the system 10 may include a vent plug. In some embodiments, the vent plug may be coupled to one of the first port 29 and the second port 30, and a particular needleless connector may be coupled to another of the first port 29 and the second port 30. In some embodiments, the system 10 may be pre-assembled as illustrated in FIG. 1A such that the user removes the system 10 illustrated in FIG. 10 from a package.

Figure 1B:
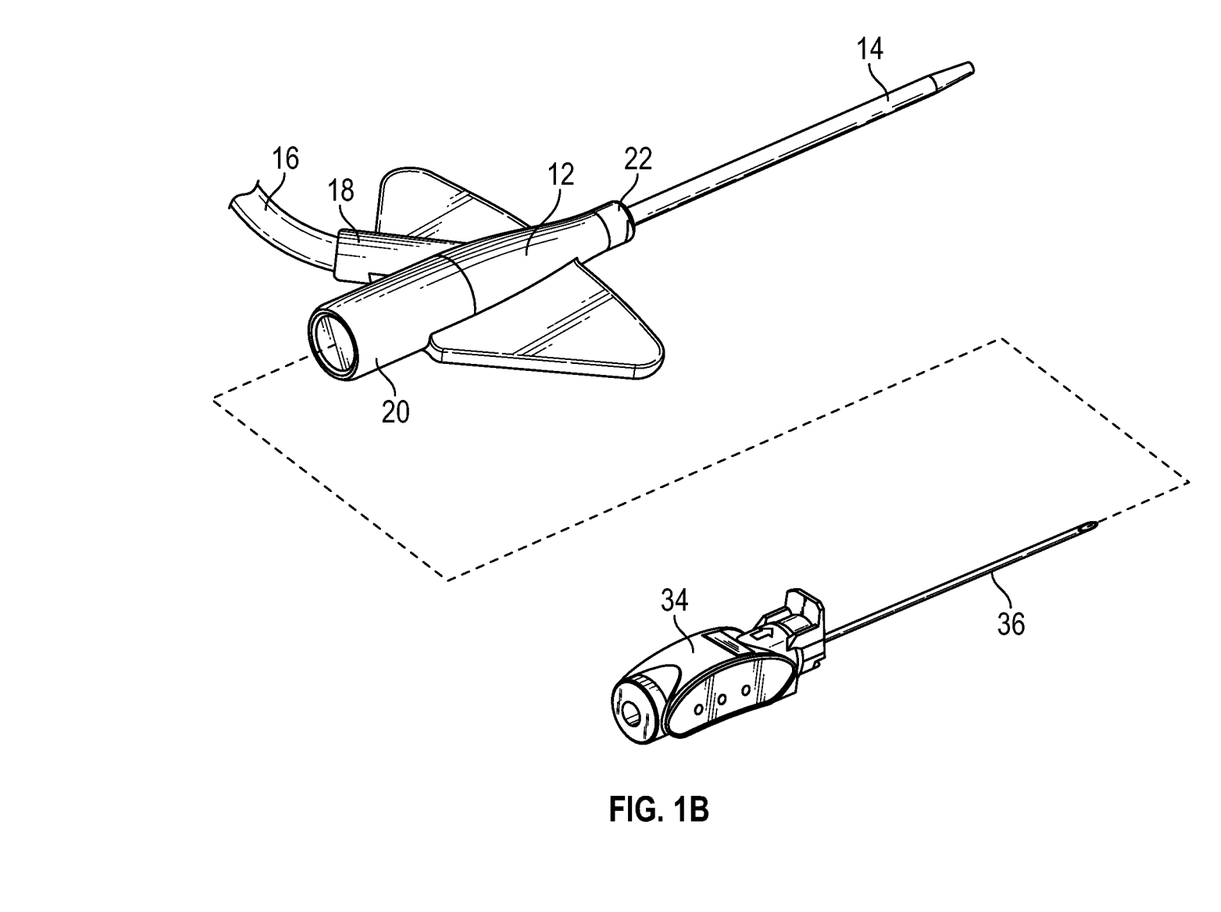
FIG. 1B is an exploded view of the needle assembly and the catheter assembly, according to some embodiments.

Referring now to FIGS. 1A-1B, in some embodiments, the needle assembly may not include a safety mechanism. In some embodiments, the needle assembly may include a safety mechanism (not illustrated), which may shield the sharp, distal tip 38 of the introducer needle 36 in response to the needle assembly being removed from the system 10. The safety mechanism may include any safety mechanism configured to shield the sharp, distal tip 38.

The safety mechanism may be coupled to the catheter adapter 12 in any number of ways. In some embodiments, the safety mechanism may include a spring mechanism. In some embodiments, the safety mechanism may be similar to that of the BD INSYTE™ AUTOGUARD™ BC Shielded IV Catheter. In some embodiments, the safety mechanism may include an internal interlock in which the safety mechanism is coupled to an internal surface of a catheter adapter 12. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter 14, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled to an external surface of the catheter adapter 12. In some embodiments, the safety mechanism may be coupled to an external surface of the catheter adapter and an internal and/or external surface of the needle hub 34. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter 12.

Figure 1C:
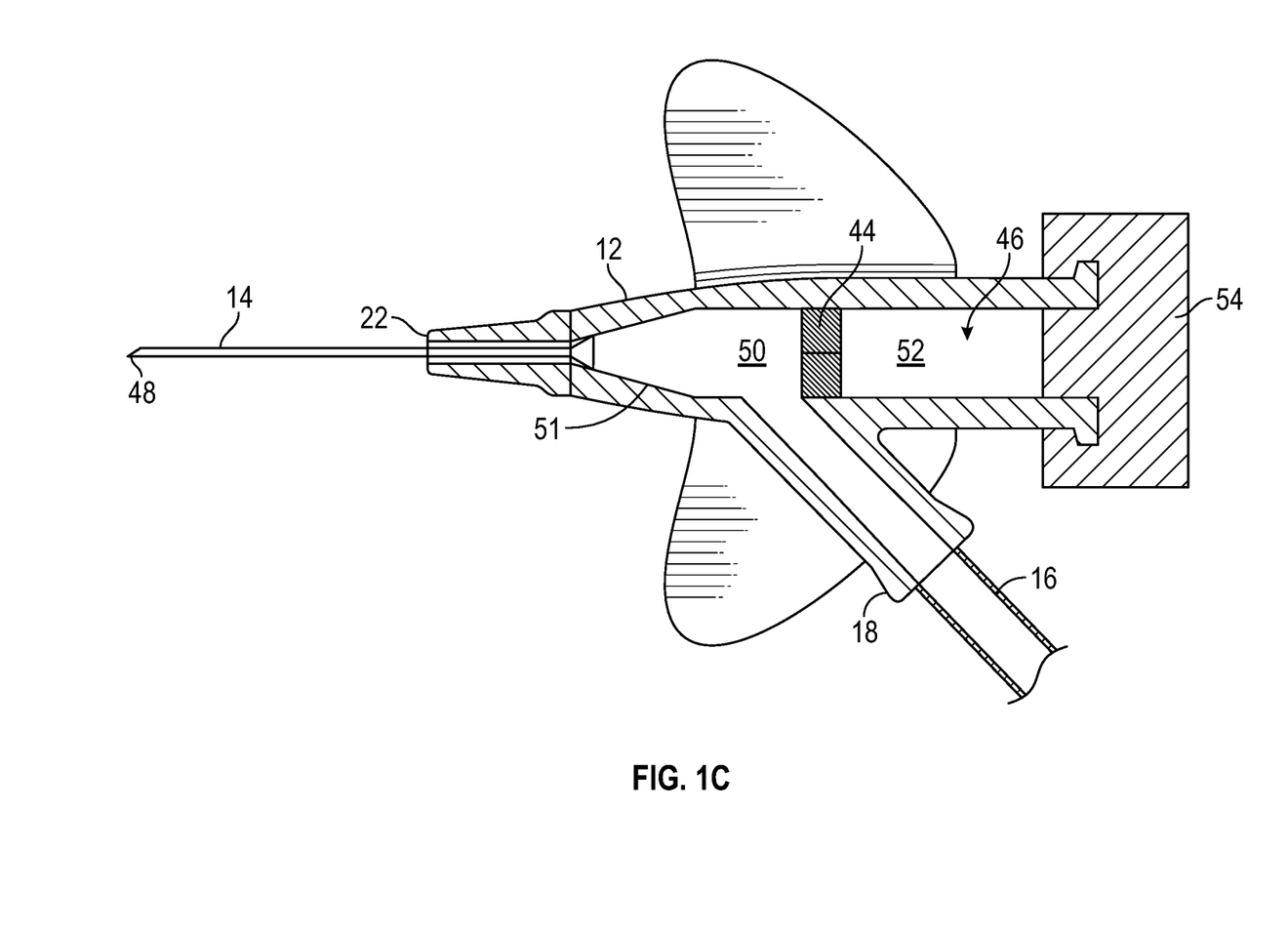
FIG. 1C is a cross-sectional view of the catheter assembly, illustrating an example blood control valve disposed proximal to an example side port, according to some embodiments.

Referring now to FIG. 1C, in some embodiments, a blood control septum or valve 44 may be disposed in the lumen 46 of the catheter adapter 12. In some embodiments, the blood control valve 44 may be single-use or multi-use. In some embodiments, the blood control valve 44 may provide a physical barrier to control the flow of blood and other fluids between a distal chamber 50 and the proximal chamber 52 of the catheter adapter 12. For example, upon insertion of the distal tip 38 of the introducer needle 36 and the distal tip 48 of the PIVC 14 into the patient's vein and the removal of the needle 50, blood from the patient may flow through the PIVC 14 and into the distal chamber 50, but may be prevented from bypassing the blood control valve 44. In some embodiments, the blood control valve 44 may be secured within the lumen 46 of the catheter adapter 12 in any number of ways, including, for example, an annular groove, adhesive, plastic weld, retainer clip, mechanical connection, etc.

In some embodiments, the blood control valve 44 may include any structural configuration that is capable of dividing the lumen 46 into the distal chamber 50 and the forward chamber 52. In some embodiments, the blood control valve 44 may include a membrane. In some embodiments, the blood control valve 44 may include a disc. In some embodiments, the blood control valve 44 may include one or more slits, which form a pathway through the blood control valve 44. In some embodiments, the blood control valve 44 may constructed of a material that is resilient and elastic.

In some embodiments, the blood control valve 44 may differ from a septum of one or more of the following in one or more ways: the BD NEXIVA™ Closed IV Catheter System, the BD CATHENA™ Catheter System, and the BD INSYTE™ AUTOGUARD™ BC Shielded IV Catheter. In the BD NEXIVA™ Closed IV Catheter System, the septum may include a distal piece having a first barrier against blood flow and a proximal piece having a second barrier against blood flow. The septum of the BD NEXIVA™ Closed IV Catheter System may be disposed within a canister and/or constructed of polyisoprene.

In some embodiments, the blood control valve 44 may be disposed proximal to the side port 18. In further detail, in some embodiments, the blood control valve 44 may be disposed proximal to an opening of the side port 18 into the lumen 46. In these and other embodiments, the blood control valve 44 may not allow air venting such that air is not permitted to pass between the distal and proximal chambers 50, 52, which may prevent blood and/or priming fluid leakage.

In some embodiments, the blood control valve 44 may allow air venting, which may facilitate observation of blood flashback by the user. In some embodiments, the blood control valve 44 may allow air venting in any number of ways. For example, an outer surface of the blood control valve 44 may include one or more grooves permeable to air but not fluid. As another example, an inner surface of the catheter adapter 12 disposed along a length of the blood control valve 44 may include one or more grooves permeable to air but not fluid. In these embodiments, the blood control valve 44 may not be permeable to fluid when in a closed position.

In some embodiments, a distal portion of the lumen 46 of the catheter adapter 12 may be narrowed to provide a guide feature 51 for the instrument as the instrument is advanced distally.

Figure 1D:
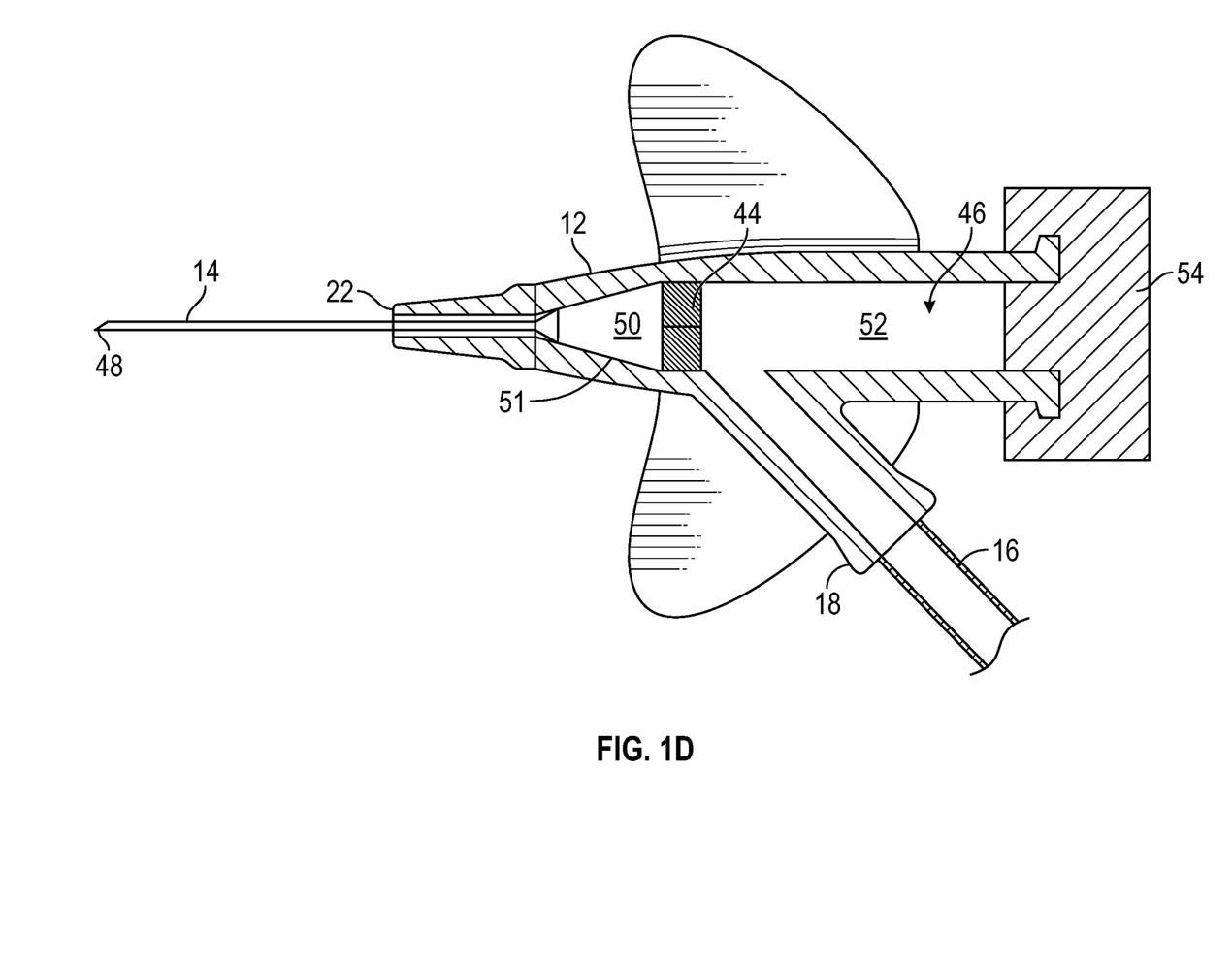
FIG. 1D is another cross-sectional view of the catheter assembly, illustrating the blood control valve disposed distal to the side port, according to some embodiments.

Referring now to FIG. 1D, in some embodiments, the blood control valve 44 may be disposed distal to the side port 18. In further detail, in some embodiments, the blood control valve 44 may be disposed distal to the opening of the side port 18 into the lumen 46. In these and other embodiments, the blood control valve 44 may allow air venting.

Referring now to both FIGS. 1C-1D, in some embodiments, the system 10 may include a cap 54, which may be coupled to the proximal end 20 of the catheter adapter 12 to seal the proximal end 20 of the catheter adapter 12 to both air and fluid.

Figure 1E:
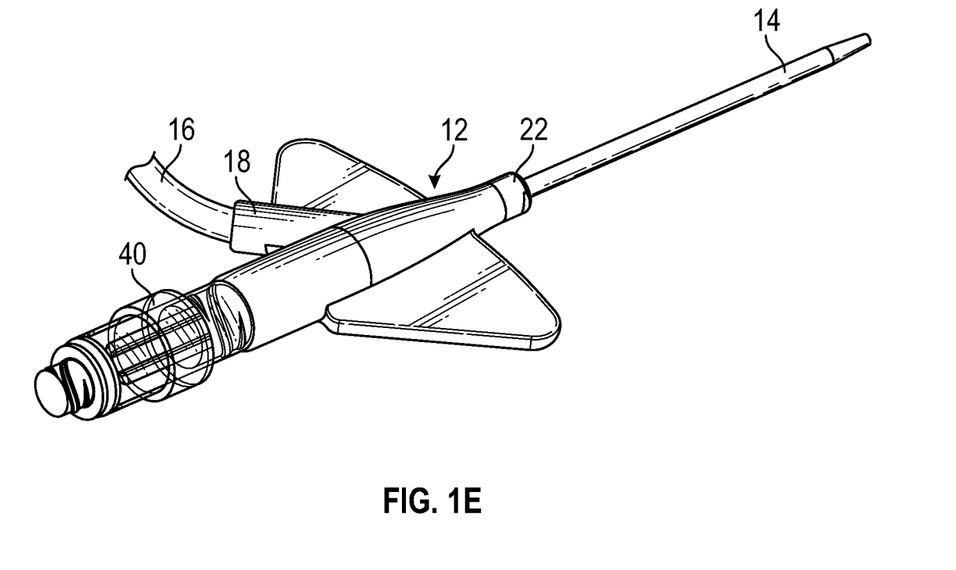
FIG. 1E is an upper perspective view of an example needleless connector coupled to the proximal end of the catheter assembly, according to some embodiments.

Referring now to FIG. 1E, in some embodiments, the system 10 may include a needleless connector 40 coupled to the proximal end 20 of the catheter adapter 12.

Figure 2A:
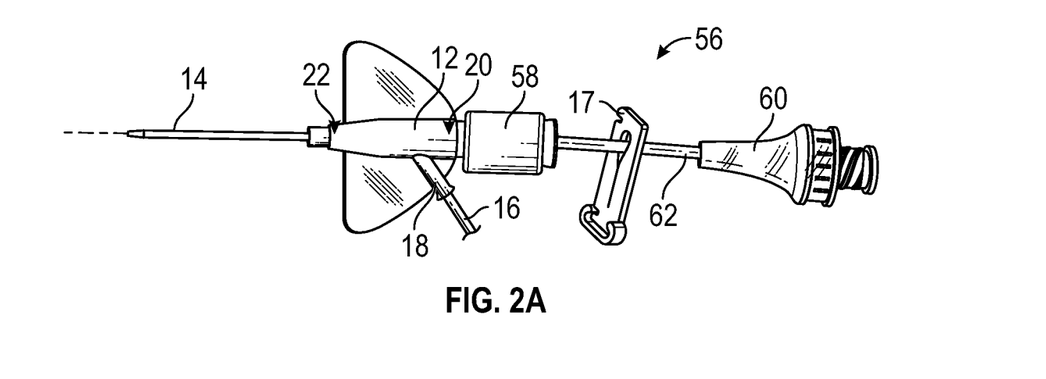
FIG. 2A is an upper perspective view of an example extension set coupled to the proximal end of the catheter assembly, according to some embodiments.

Referring now to FIG. 2A, in some embodiments, an extension set 56 may be coupled to the proximal end 20 of the catheter adapter 12. In some embodiments, the proximal end 20 of the catheter adapter 12 may include a luer adapter, such as, for example, a slip or thread male or female luer adapter, or a non-luer adapter. In some embodiments, the extension set 56 may include a distal connector 58 coupled to the proximal end 20 of the catheter adapter, and a proximal connector 60.

In some embodiments, the extension set 56 may include tubing 62 disposed between the distal connector 58 and the proximal connector 60. In some embodiments, the tubing 62 may include a clamp 17. In some embodiments, a distal end of the tubing 62 may be secured within the distal connector 58, and a proximal end of the tubing 62 may be secured within the proximal connector 60. In some embodiments, the proximal connector 60 may include a needleless connector 40. In some embodiments, the distal connector 58 and/or the proximal connector 60 may include a luer adapter, such as, for example, such as a slip or thread male or female luer adapter, or a non-luer adapter.

In some embodiments, the tubing 62 may be rigid, semi-rigid, or flexible. In some embodiments, one or more of the following may form a straight or nearly straight pathway for delivery of the instrument to the PIVC 14: the PIVC 14, the catheter adapter 12, the distal connector 58, the proximal connector 60, and the tubing 62. In some embodiments, the straight or nearly straight pathway may be smooth such that the instrument is prevented from disturbance by any catches, such as any sharp edges or snag points.

Figure 2B:
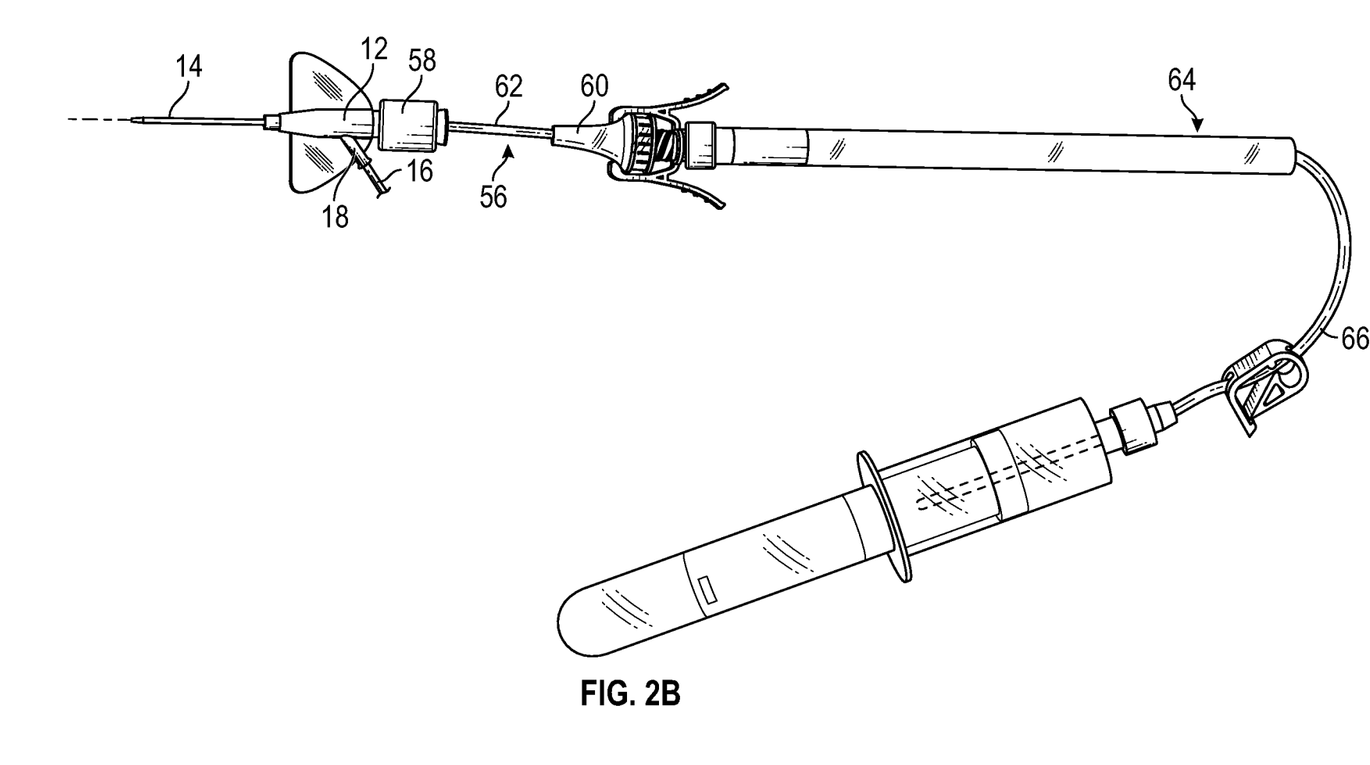
FIG. 2B is an upper perspective view of an example instrument delivery device coupled to the extension set.

Referring now to FIG. 2B, in some embodiments, the system 10 may include an instrument delivery device 64, which may be removably coupled to the proximal end 20 of the catheter adapter 12. In some embodiments, the instrument delivery device 64 may be coupled to the proximal end 20 of the catheter adapter 12 directly or via the extension set 56 or via the needleless connector 40 (such as in FIG. 1E, for example). In further detail, in some embodiments, the instrument delivery device 64 may be coupled directly to the proximal connector 60 of the extension set 56 or coupled directly to the needleless connector 40. In some embodiments, the instrument delivery device 64 may include the instrument 66, which may be configured to advance distally through the blood control valve 44 and into or through the PIVC 14. Non-limiting examples of instrument delivery devices are described in U.S. Pat. No. 9,750,446, filed Feb. 4, 2013, entitled "SYSTEMS AND METHODS FOR PHLEBOTOMY THROUGH A PERIPHERAL IV CATHETER," and U.S. Patent Application No. 62/534,552, filed Jul. 19, 2017, entitled "EXTENSION HOUSING A PROBE OR INTRAVENOUS CATHETER," which are hereby incorporated by reference. In some embodiments, a blood collection device may be coupled to a proximal end of the instrument 66.

Figure 2C:
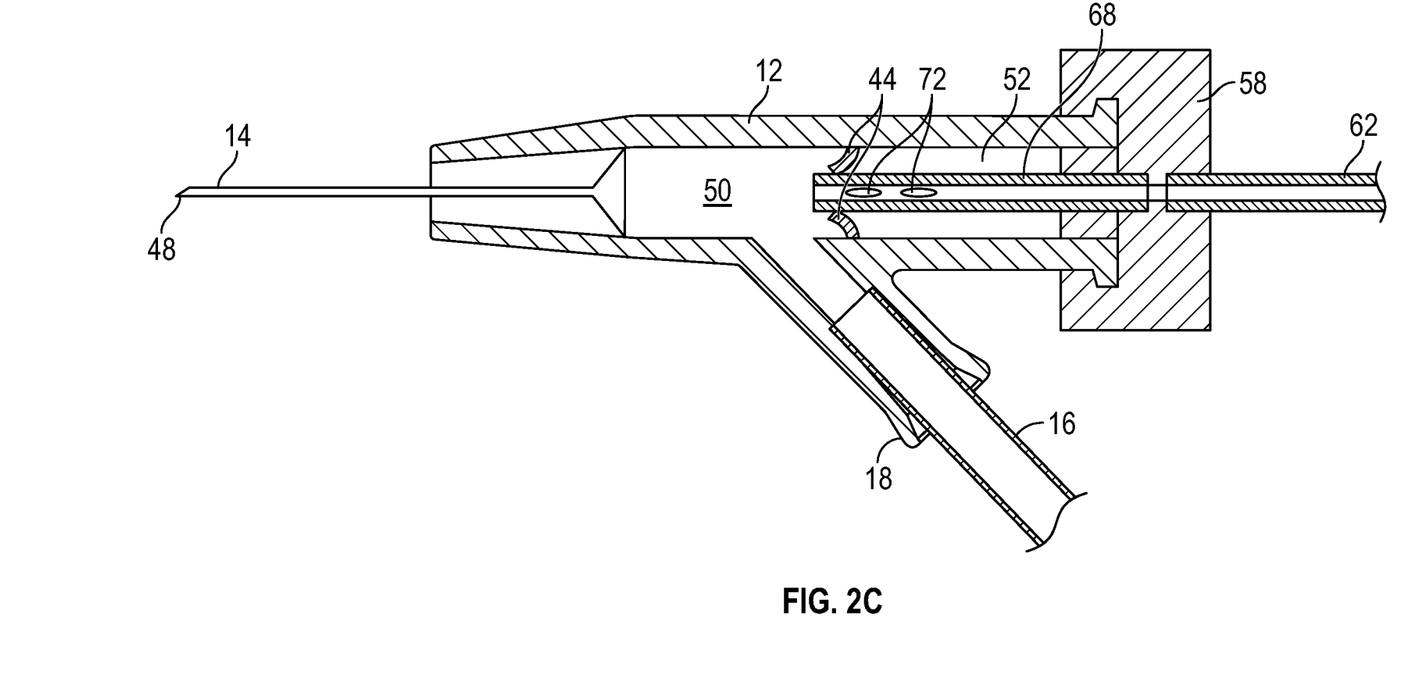
FIG. 2C is a cross-sectional view of an example distal connector of the extension set coupled to the proximal end of the catheter assembly, according to some embodiments.

Referring now to FIG. 2C, in some embodiments, the distal connector 58 may include a cannula 68 that penetrates the blood control valve 44 in response to the distal connector 58 being coupled to the proximal end 20 of the catheter adapter 12. In some embodiments, the cannula 68 may be blunt. In some embodiments, the cannula 68 may be constructed of plastic or metal, such as, for example, steel. In some embodiments, the cannula 68 may include one or more flushing windows 72 through which fluid may travel.

Figure 2D:
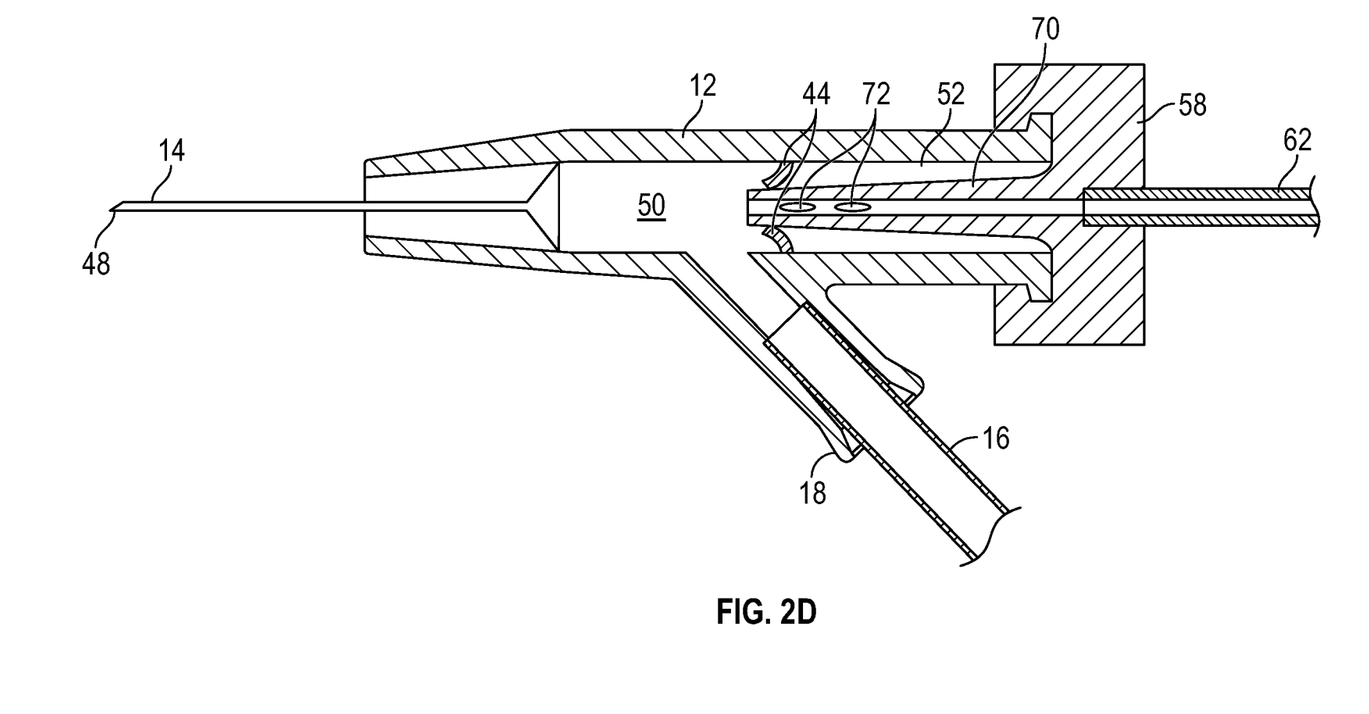
FIG. 2D is a cross-sectional view of another example distal connector of the extension set coupled to the proximal end of the catheter assembly, according to some embodiments.

Referring now to FIG. 2D, in some embodiments, the distal connector 58 may include a male luer, which may include an extension 70 or modified tip. In some embodiments, the extension 70 may penetrate the blood control valve 44 in response to the distal connector 58 being coupled to the proximal end 20 of the catheter adapter 12. In some embodiments, the extension 70 may include one or more flushing windows 72 through which fluid may travel. In some embodiments, the cannula 68 of FIG. 2C and the extension 70 of FIG. 2D may each correspond to an actuator of the blood control valve. In some embodiments, the lumen 46 of the catheter adapter 12 may not include an actuator of the blood control valve other than the cannula 68 or the extension 70. In further detail, in some embodiments, the lumen 46 of the catheter adapter 12 may not include an actuator of the blood control valve when the distal connector 58 is not coupled to the catheter adapter 12. It is understood that in some embodiments, the male luer having the cannula 68 or the extension 70 may be part of a particular instrument, the distal connector 58, or the needleless connector 40.

Figure 2E:
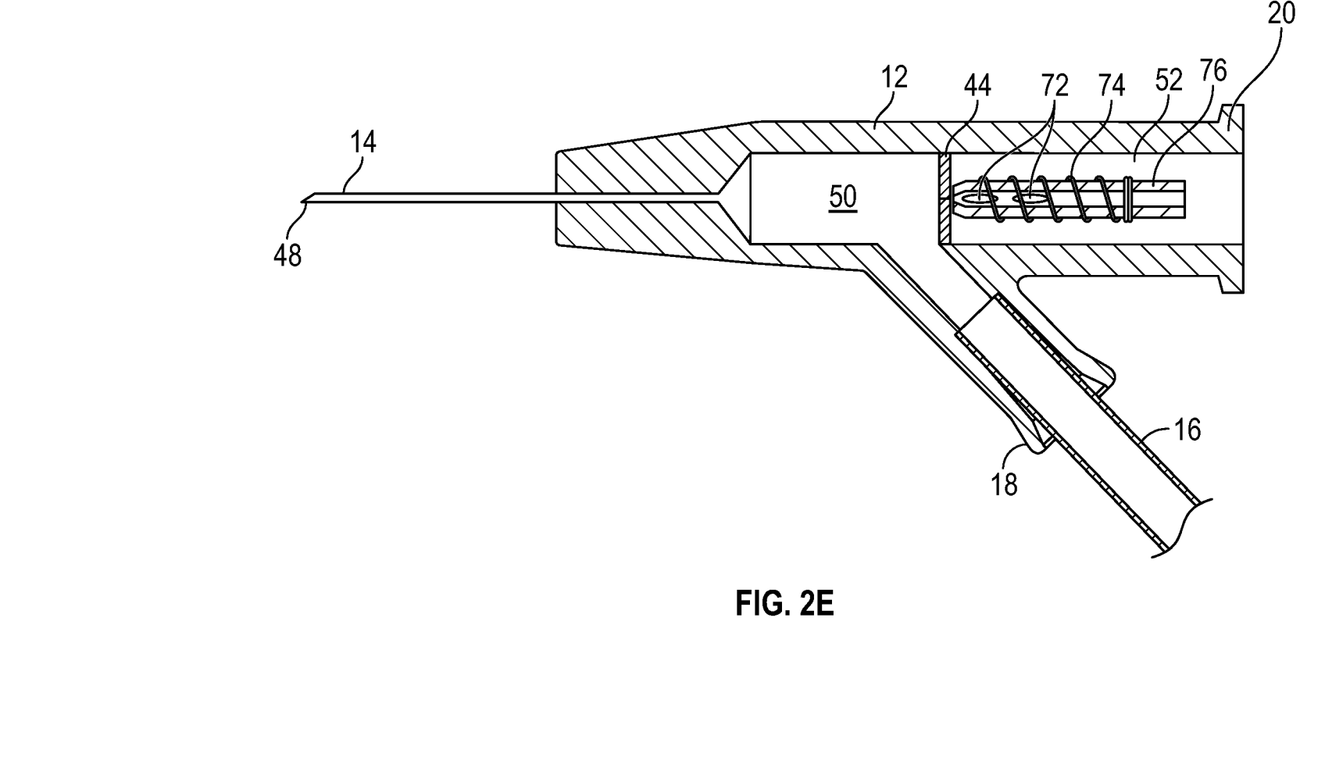
FIG. 2E illustrates an example actuator prior to coupling of the distal connector to the proximal end of the catheter assembly, according to some embodiments.
Figure 2F:
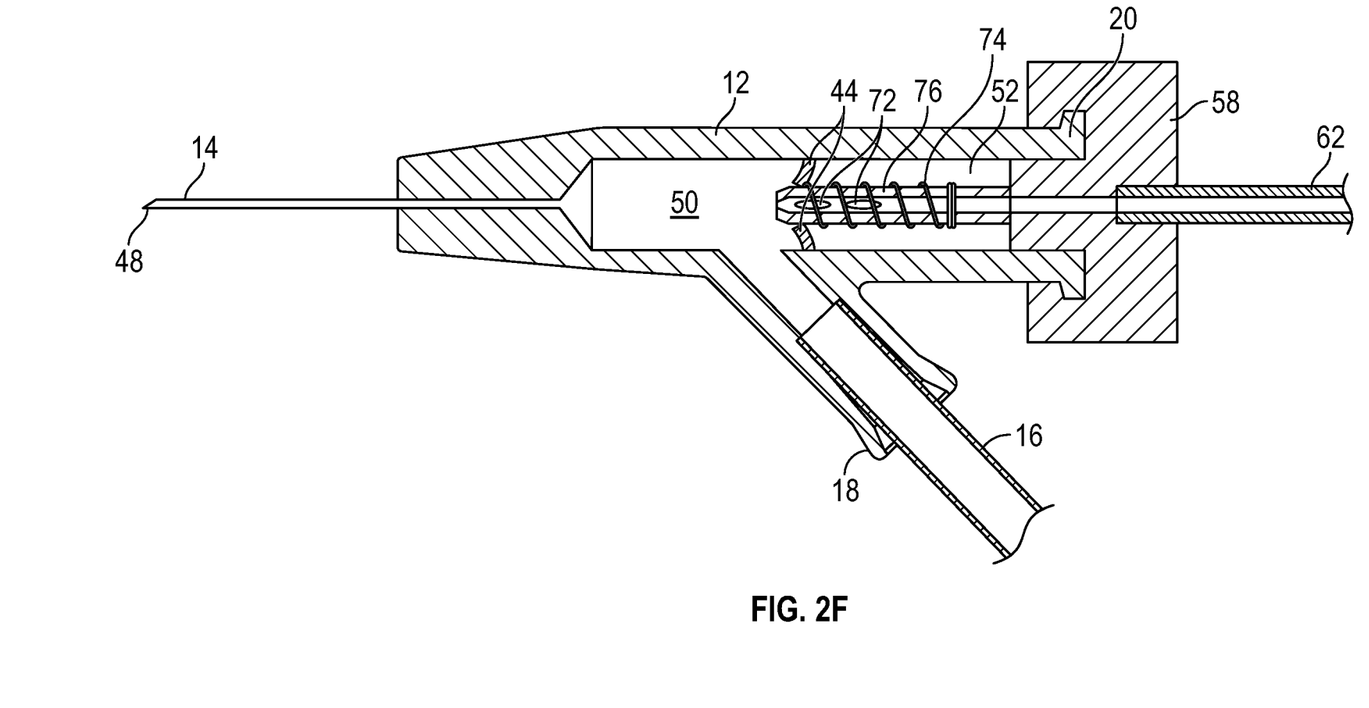
FIG. 2F illustrates the actuator penetrating the blood control valve, according to some embodiments.

Referring now to FIG. 2E-2F, in some embodiments, the lumen 46 of the catheter adapter 12 may include an actuator 76, which may penetrate the blood control valve 44 in response to coupling of the distal connector 58 to the proximal end 20 of the catheter adapter 12. In some embodiments, the actuator 76 may be a separate element and/or not coupled with the distal connector 58 or the needleless connector 40. In some embodiments, the actuator 76 may be positioned within the lumen 46 and may not penetrate the blood control valve 44 when the extension set 56 is removed from the catheter adapter 12. In some embodiments, the actuator 76 may not be present when the distal connector 58 includes the male luer having the extension 70 or the cannula 68. In some embodiments, the actuator 76 may include one or more flushing windows 72 through which fluid may travel.

In some embodiments, the system 10 may include one or more means of returning the actuator 76 to an unactuated position, allowing the blood control valve 44 to close and seal. For example, the blood control valve 44 may provide a restoring force to move the actuator 76 proximally to the unactuated position.

As another example, the lumen 46 of the catheter adapter 12 may include a spring 74 and the actuator 76. In some embodiments, the actuator 76 may be attached to the spring 74. In some embodiments, when a male luer is connected to the catheter adapter 12, the actuator 76 may be pushed distally and may open a slit of the blood control valve 44, allowing infusion or blood draw. In some embodiments, the spring 74 may be unactuated or compressed in response to contact from the male luer. In some embodiments, when the male luer is disconnected from the catheter adapter 12, the spring 74 may be actuated and may push the actuator 76 back in the proximal direction, thus closing the slit of the blood control valve 44 and sealing the fluid path. In some embodiments, the distal connector 58 of the extension set 56 may include the male luer. In some embodiments, the needleless connector 40 may include the male luer. In some embodiments, a particular instrument, such as, for example, the instrument 66, may include the male luer.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A system for facilitating instrument delivery through a peripheral intravenous catheter, comprising:
   a catheter adapter comprising an integrally formed body having a proximal end, a distal end, and a lumen extending there through, the catheter adapter having a side port;
   an extension tube extending from the side port;
   a blood control valve disposed in the lumen of the integrally formed body of the catheter adapter, wherein the blood control valve is disc-shaped and configured to vent air when closed, wherein a proximal end of the blood control valve is distal to the side port, wherein in response to coupling of a distal connector to the proximal end of the catheter adapter, the blood control valve is configured to be opened by a cannula of the distal connector, wherein the lumen of the catheter adapter does not include a separate actuator; and
   a peripheral intravenous catheter extending distally from the catheter adapter.

2. The system of claim 1, further comprising:
   a Y-adapter coupled to a proximal end of the extension tube, the Y-adapter having a first port and a second port;
   a needleless connector coupled to the first port; and
   a needleless connector coupled to the second port.

3. The system of claim 1, further comprising a cap coupled to the proximal end of the catheter adapter.

4. The system of claim 1, further comprising a needleless connector coupled to the proximal end of the catheter adapter.

5. The system of claim 1, further comprising an extension set, the extension set comprising:
   a distal connector coupled to the proximal end of the catheter adapter, wherein the distal connector comprises a cannula that penetrates the blood control valve in response to the distal connector being coupled to the proximal end of the catheter adapter;
   a proximal connector; and
   tubing disposed between the distal connector and the proximal connector.

6. The system of claim 5, wherein the proximal connector comprises a needleless connector.

7. The system of claim 5, wherein the cannula is blunt and constructed of plastic or steel.

8. The system of claim 5, wherein the cannula comprises a plurality of flushing windows.

9. The system of claim 1, further comprising an extension set coupled to the proximal end of the catheter adapter, the extension set comprising:
   a distal connector coupled to the proximal end of the catheter adapter, wherein the distal connector comprises a male luer;
   a proximal connector; and
   tubing disposed between the distal connector and the proximal connector.

10. The system of claim 9, wherein the proximal connector comprises a needleless connector.

11. The system of claim 1, further comprising the distal connector coupled to the proximal end of the catheter adapter, wherein the distal connector comprises a male luer having the cannula penetrating the blood control valve.

12. The system of claim 9, further comprising an instrument delivery device coupled to the proximal end of the catheter adapter, wherein the instrument delivery device comprises an instrument configured to advance distally through the blood control valve and the peripheral intravenous catheter, wherein the instrument comprises a guidewire, a probe with a sensor, tubing for fluid infusion or blood draw or a light tube for disinfection.

13. The system of claim 1, further comprising a needle assembly removably coupled to the proximal end of the catheter adapter, an introducer needle of the needle assembly extending through the blood control valve.

14. The system of claim 1, wherein the proximal end of the catheter adapter comprises a luer adapter.

15. The system of claim 1, wherein the proximal end of the catheter adapter comprises a non-luer adapter.

16. The system of claim 1, wherein a distal portion of the lumen is narrowed to provide a guide feature.

* * * * *